United States Patent [19]

Taff et al.

[11] Patent Number: 4,643,172

[45] Date of Patent: Feb. 17, 1987

[54] LUMINESCENT TONGUE DEPRESSOR

[76] Inventors: Barry E. Taff, 8665 Pickford St. #8, Los Angeles, Calif. 90035; Kenneth P. Stoller, 2919 N. Lake Ave., Altadena, Calif. 91001

[21] Appl. No.: 789,417

[22] Filed: Oct. 21, 1985

[51] Int. Cl.⁴ .................... A61B 13/00; A61B 1/24
[52] U.S. Cl. ................................. 128/16; 362/804
[58] Field of Search .............. 128/16, 11, 13, 15; 362/120, 804

[56] References Cited

U.S. PATENT DOCUMENTS

| | | | |
|---|---|---|---|
| 1,078,167 | 11/1913 | Robnett | 128/16 |
| 3,349,764 | 10/1967 | Edinger et al. | 128/16 |
| 3,426,749 | 2/1969 | Jephcott | 128/11 |
| 3,638,644 | 2/1972 | Reick | 128/16 |

Primary Examiner—William H. Grieb
Attorney, Agent, or Firm—Philip D. Junkins

[57] ABSTRACT

A luminescent tongue depressor having a luminiferous depressor element connected to a handle. Means to illuminate the depressor element is preferably a monatomic gas contained within a vacuum tube positioned within the handle element of the device. A concave reflector element directs and concentrates the light towards the depressor element. A rechargeable power source electrically connected to the sealed vacuum tube acts to provide light to the depressor element and its surrounding area. Light dispersing grooves in the depressor element act to disperse the light transmitted from the light source through the depressor element in the mouth. In an alternative embodiment of the device, the depressor element pivots to lie substantially flat against the base of the handle element when not in use.

16 Claims, 5 Drawing Figures

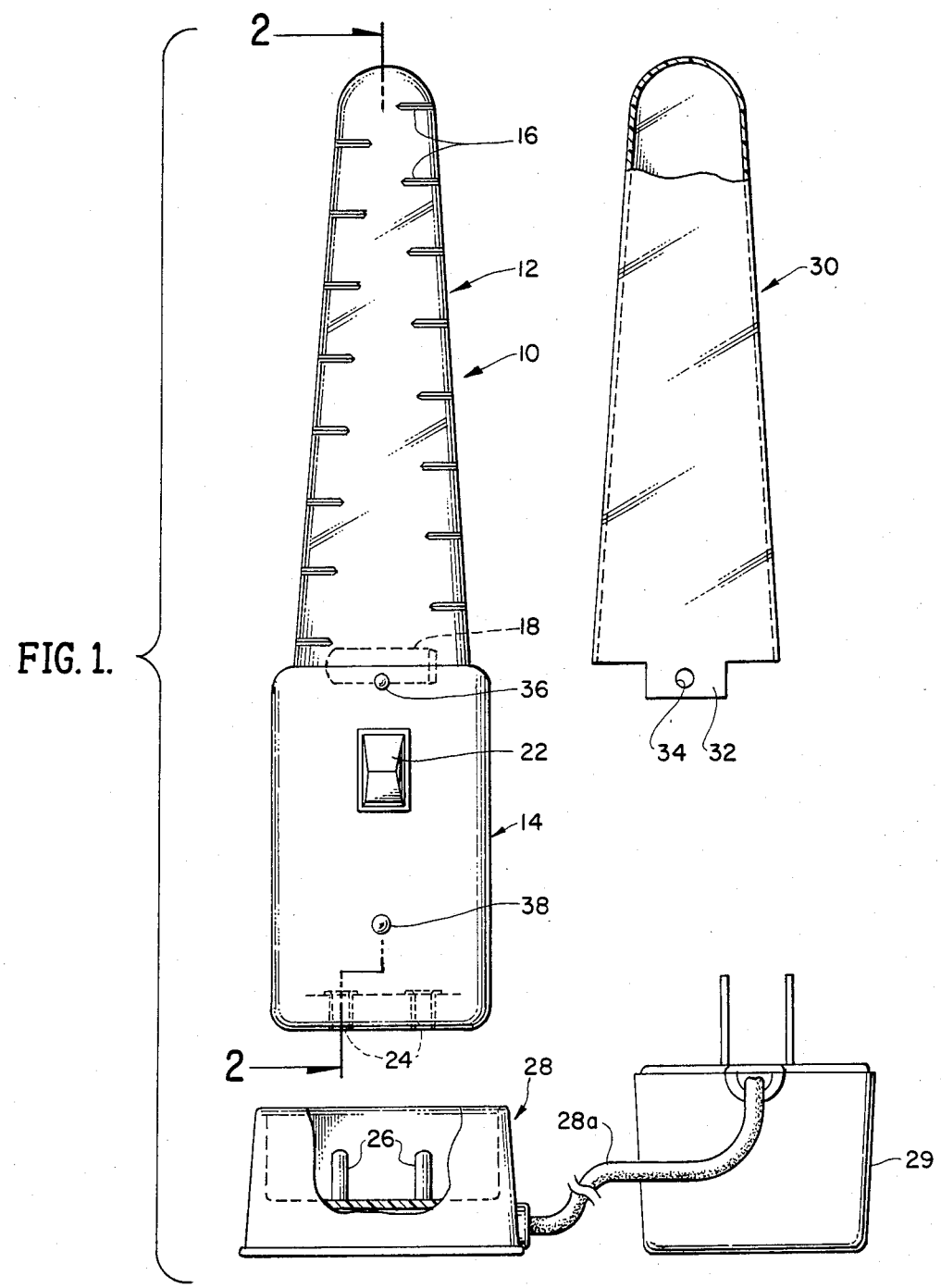
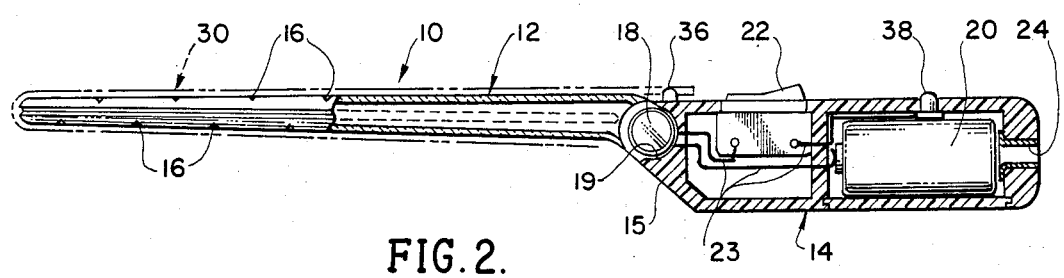
FIG. 1.
FIG. 2.

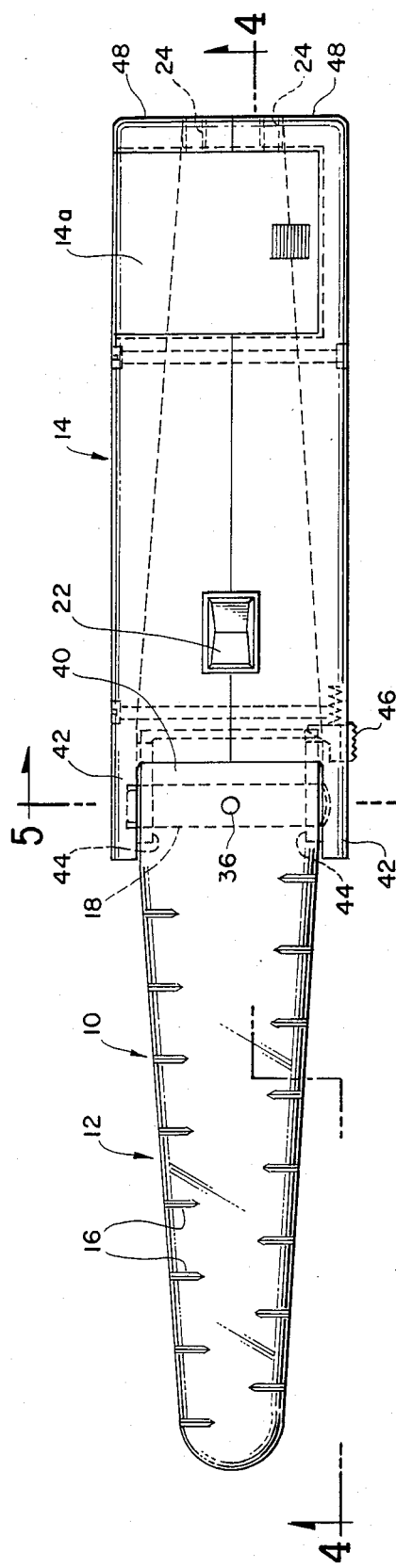
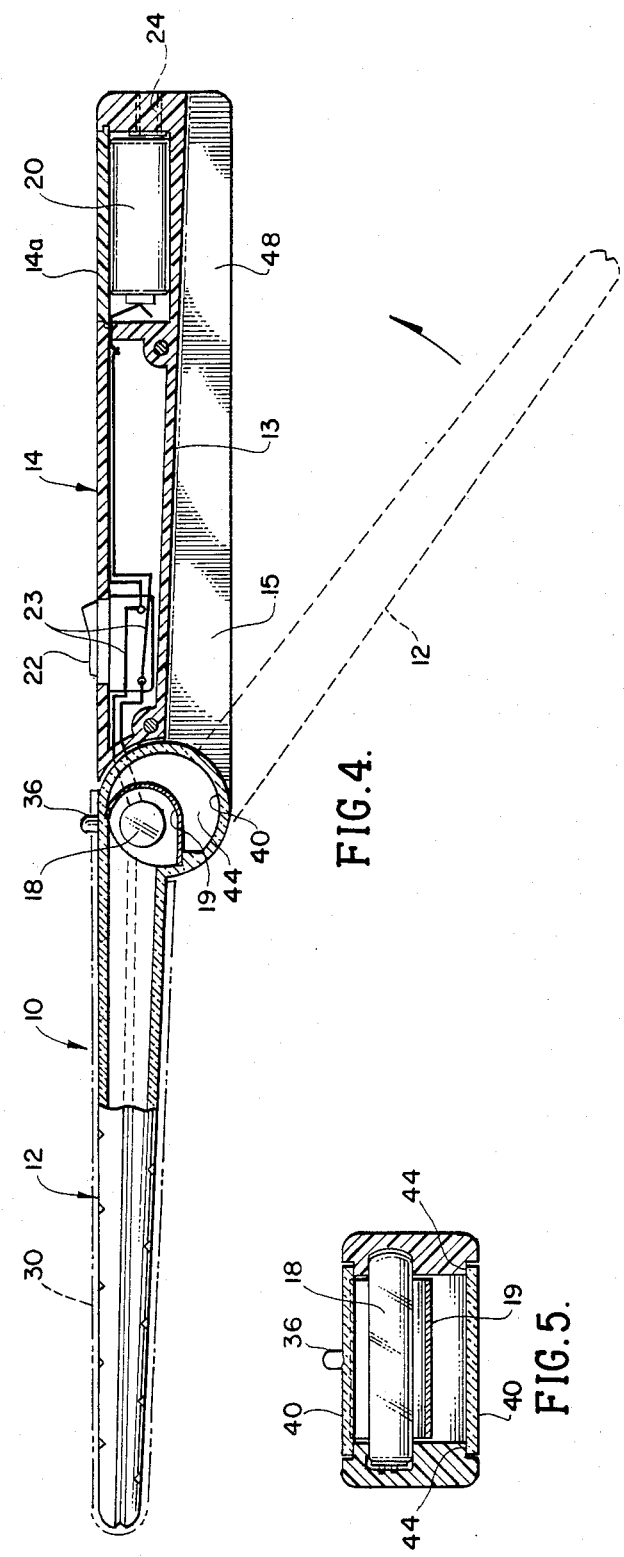
FIG. 3.
FIG. 4.
FIG. 5.

LUMINESCENT TONGUE DEPRESSOR

BACKGROUND OF THE INVENTION

The field of the invention is medical instruments, and more particularly, medical instruments used by medical personnel in examining the mouth and upper throat regions of the body.

In order to adequately examine the mouth and upper throat regions of the body, including the tonsils, it is necessary for medical personnel to use instruments to depress or move aside the tongue. In addition, it is necessary for medical personnel to use some sort of external non-monochromatic light source in order to adequately illuminate the relevant areas of the mouth and upper throat.

Traditionally, tongue depressors are made from a fibrous material such as wood and are held in one hand by the medical examiner. These devices are usually discarded after a single use in conjunction with the patient's examination. Light is typically provided by a small flashlight held in the medical examiner's other hand. Thus, both hands of the person performing the examination are tied up, thereby limiting other procedures or checks which may be simultaneously performed by the medical examiner. In addition, some patients complain of distaste or discomfort resulting from the use of fibrous tongue depressors.

SUMMARY OF THE INVENTION

The luminescent tongue depressor described herein is constructed so as to allow the person performing the medical examination to have one hand free during examination of the mouth and upper throat area, while still retaining the ability to depress or otherwise move the tongue aside and provide adequate light to make the examination. The device preferably has a smooth sheath member made from either a rigid or flimsy material which may be either sanitized or discarded after completing the examination of the patient. Such a sheath member avoids patient complaints of distaste and discomfort caused by the fibrous nature of traditional tongue depressors.

The device is free of electrical connections so as to avoid any possibility of electrical shock to either the medical examiner or the patient. Light dispersing grooves are preferably formed in the depressor element to disperse light, thereby making applicant's device substantially omniluminescent. In a second embodiment of applicant's device, the depressor element maybe rotated about the handle element such that the device may be conveniently carried and stored when not in use.

It is therefore an object of the invention to provide a means for examining the mouth and upper throat area of a patient which will allow medical personnel to simultaneously illuminate the mouth and upper throat area and depress or otherwise move aside the tongue while using only one hand.

It is a further object of the invention to provide a luminescent tongue depressor which will avoid the danger of possibly electrocuting either the medical personnel undertaking or the patient undergoing the examination.

It is a further object of the invention to provide a luminescent tongue depressor which is substantially omniluminescent.

It is a further object of the invention to provide a luminescent tongue depressor which may be conveniently carried and stored by medical personnel.

It is a further object of the invention to avoid patient discomfort and distaste resulting from the fibrous nature of traditional tongue depressors.

It is a further object of the invention to provide a luminescent tongue depressor with a removable sheath means which may be either sanitized or discarded. Other and more detailed objects of the invention shall become apparent upon examination of the description and drawings contained herein.

DESCRIPTION OF THE DRAWINGS

FIG. 1 is an exploded view of a tongue depressor, disposible sheath means and storage stand of the invention;

FIG. 2 is a cross sectional view taken along line 2—2 of FIG. 1;

FIG. 3 is a top view showing a second embodiment of the invention;

FIG. 4 is a cross sectional view taken along line 4—4 of FIG. 3; and

FIG. 5 is a cross sectional view taken along line 5—5 of FIG. 3.

DETAILED DESCRIPTION OF THE INVENTION

Referring to FIGS. 1 and 2, a first embodiment of the invention comprises luminescent tongue depressor 10 which has a depressor element 12 and a handle element 14. The depressor element 12 is constructed of a luminiferous material such as a transparent polycarbonate material, for example, the material sold by the General Electric Co. under the trademark LEXAN.

In addition, the depressor element is preferably hollow in construction and has light dispersing grooves 16 in its upper, lower and circumferential surfaces. The grooves 16 act to refract and disperse the light transmitted through the depressor element 12 so as to make the device substantially omniluminescent. Such a device provides greater illumination in and around the area of the depressor element 12.

A vacuum tube 18 containing a monatomic gas such as Xenon is positioned near the junction between the handle element 14 and the depressor element 12. The vacuum tube 18 is electrically connected to a rechargeable power supply 20 such as a cadmium-nickel or lead-acid rechargeable battery. When, for example, the Xenon gas in the vacuum tube is subjected to an electrical potential, the energized Xenon gas acts as a multichromatic light source. A concave reflector element 19 is positioned between the vacuum tube 18 light source and the depressor element 12 to insure that the light is directed and concentrated in the direction of the depressor element 12.

A multi-positionable switching means 22 acts to open or close the circuit 23 between the rechargeable power supply 20 and the sealed vacuum tube 18, thereby energizing or de-energizing the light source. In view of the small amount of electrical energy contained within the rechargeable power supply 20, and the absence of any connection to a continuous large electrical power supply, such as a wall socket, both the medical examiner using the device and the patient undergoing examination are protected from injury due to electrical work should the device malfunction.

The handle element 14 is further provided with a plug socket means 24 adapted to receive a recharge plug 26 contained, for example in the device storage stand 28. The recharge plug 26 may be electrically connected through power cord 28a and transformer 29 to a continuous source of electrical power (not shown) thereby recharging the device when not in use. Moreover, the handle element 14 is advantageously shaped with a tapered front edge 15 to make the device easier to grip and use by medical personnel.

A removable sheath means 30 is provided to protect the depressor element 12. The sheath means 30 may be constructed from either a rigid or flimsy material which is either sanitized or discarded after examination of a patient. As shown in FIG. 1, the preferred embodiment of the sheath means 30 is made from a rigid plastic material and has a tab member 32 with a pin receptacle 34 therethrough.

When using the tongue depressor of the invention, the sheath means 30 is positioned about the depressor element 12 such that the pin receptacle 34 in the tab member 32 engages with a pin member 36 on the handle element 14 of the tongue depressor 10. When it is desired to change the sheath means 30, the tab member 32 is raised, thereby releasing the sheath means from engagement with the tongue depressor 10. The sheath means 30 may be either discarded or sanitized and reused.

Additionally, the preferred embodiment of the device is provided with a means for testing the power in the rechargeable power supply 20. So constructed, when the multi-positionable switch 22 is moved to a designated position, a small light means such as a light emitting diode 38, will glow, thereby indicating to the user that adequate power remains in the rechargeable power supply 20.

As shown in FIGS. 3, 4 and 5 a second embodiment of the device of the invention is constructed such that the depressor element 12 may pivot about the handle element 14. In such an embodiment, the depressor element 12 has a hollow rear cylindrical portion 40. Arms 42 extend forward from the sides of the handle element 14 and are connected to the ends of the cylindrical portion 40 so as to allow the depressor element 12 to rotate within the handle element 14 by means of the annular shoulders or truncated sleeves 44. When assembled, the annular shoulders or truncated sleeves 44 act as the bearing surface for the rotation of the cylindrical end 40 of the depressor element 12. In the particular embodiment shown in FIGS. 3, 4 and 5, the vacuum tube 18 and the concave reflector element 19 are positioned within the hollow cylindrical portion 40 of the depressor element 12. The reflector 19 snaps into place in the hollow portion 40.

In addition, a spring-loaded catch mechanism 46 acts to lock the depressor element 12 in either the extended or rotated position. Complete rotation of the depressor element 12 to a position substantially parallel to the bottom of the handle element 14 is facilitated by making the lower frontal section 15 of the handle element 14 substantially open such as shown in FIG. 4. Further, the base 13 of the handle portion 14 is tapered such as that shown in FIG. 4 so that the depressor element 12 may be conveniently stored in the handle element 14. The depressor element 12 is further protected when in the rotated position by extensions 48 extending downward from the handle element 14 to substantially enclose the rotated depressor element 12 on two sides. Access to the power supply 20 is provided through the sliding and removable closure panel 14a in the handle element 14.

Having described the preferred embodiment of the invention, Applicants contemplate that additional modifications may be made hereto without departing from the nature or spirit of the invention. For example, modifications to the means for connecting a sheath member 30 to the tongue depressor 10 or modifications to the tongue depressor such that the depressor element 12 and the handle element 14 are combined into a single unitary element using the same or other known means for providing non-monochromatic illumination or connecting the pivoting depressor element of Applicant's second embodiment to the handle element by a ratchet mechanism or the like may be accomplished hereunder. Therefore, the embodiments of the invention described hereinabove are intended for purposes of example only and should not be construed to limit the scope of the claims appended hereto.

We claim:

1. A luminescent tongue depressor assembly comprising: an elongated luminiferous depressor element having light dispersing grooves formed therein, said depressor element having a handle portion at one end thereof; means to illuminate said depressor element including a vacuum tube proximate said handle portion and containing a monatomic gas and means to electrically energize said gas in said tube and thereby generate light; means to concentrate and direct said light toward and through said depressor element; and removable sheath means to protect said depressor element.

2. A luminescent tongue depressor assembly as set forth in claim 1 wherein said means to electrically energize said monatomic gas includes a rechargeable battery positioned within said handle portion.

3. A luminescent tongue depressor assembly as set forth in claim 1 wherein said removable sheath means is rigid.

4. A luminescent tongue depressor assembly as set forth in claim 1 wherein the handle portion of said depressor element is pivotally mounted to said depressor element and includes means to secure said depressor element in a selected position with respect to said handle portion.

5. A luminescent tongue depressor assembly as set forth in claim 1 wherein said depressor element is transparent and is substantially hollow.

6. A luminescent tongue depressor assembly comprising: an elongated hollow luminiferous depressor element having light dispersing grooves formed on the outer surface thereof; a handle element connected to said depressor element at one end thereof; means to illuminate said depressor element including a vacuum tube within said depressor element at its end proximate said handle element and containing a monatomic gas and means to electrically energize said gas in said tube and thereby generate light; means to concentrate and direct said light toward and into said depressor element to make said element substantially omniluminescent; and removable sheath means to protect said depressor element.

7. A luminescent tongue depressor assembly as set forth in claim 6 wherein said means to electrically energize said monatomic gas includes a rechargeable battery positioned within said handle element.

8. A luminescent tongue depressor comprising a luminiferous depressor element with light dispersing grooves formed therein, a handle element connected to said depressor element, a vacuum tube containing a monatomic gas arranged so as to illuminate said depressor element, means to electrically energize said gas, means to direct and concentrate the light towards said depressor element and removable sheath means to protect said depressor element.

9. A luminescent tongue depressor as set forth in claim 8 including pivoting means connecting said depressor element to said handle element.

10. A luminescent tongue depressor as set forth in claim 9 wherein said pivoting means includes a cylindrical portion formed on one end of said depressor element, arms extending from said handle element, annular shoulder means formed on said arms and fitted within said cylindrical portion of said depressor element.

11. A luminescent tongue depressor as set forth in claim 10 wherein said vacuum tube is fixed within said handle element arms.

12. A luminescent tongue depressor as set forth in claim 10 wherein said means to direct and concentrate the light is a substantially concave reflector element and said reflector element is fixed within said handle element arms.

13. A luminescent tongue depressor as set forth in claim 12 including means to secure said pivoting depressor element in a selected position.

14. A luminescent tongue depressor as set forth in claim 10 including extensions formed on said handle element so as to substantially enclose said depressor element on at least two sides when said depressor element is in its rotated position.

15. A luminescent tongue depressor comprising a luminiferous depressor element with light dispersing grooves formed therein, pivoting means connecting said depressor element to a handle element, said pivoting means including at least one arm extending from said handle element, a cylindrical portion formed in one end of said depressor element, truncated sleeve means formed on at least one side of each said arm and fitted within said cylindrical portion of said depressor element.

16. A luminescent tongue depressor comprising, a luminiferous depressor element with light dispersing grooves formed therein, a handle element connected to said depressor element, a vacuum tube containing a monatomic gas arranged so as to illuminate said depressor element, means to electrically energize said gas including a rechargeable battery positioned within said handle element, means to direct and concentrate the light towards the depressor element including a substantially concave reflector element, removable sheath means to protect said depressor element, a cylindrical portion formed within one end of said depressor element, arms extending from said one end of said handle element, annular shoulder means formed on said arms and fitted within said cylindrical portion of said depressor element, and means to secure said pivoting depressor element in a selected position.

* * * * *